United States Patent [19]

Watanabe et al.

[11] Patent Number: 4,680,311

[45] Date of Patent: Jul. 14, 1987

[54] METHOD FOR THE TREATMENT OF SYSTEMIC MYCOSIS

[75] Inventors: Naoharu Watanabe, Kounosu; Kazuo Numata, Ageo; Michio Yamagishi, Yoshimi; Taku Mizutani; Sadafumi Omura, both of Ageo; Hideyo Yamaguchi, Kawasaki, all of Japan

[73] Assignee: Taisho Pharmaceutical Co., Ltd., Japan

[21] Appl. No.: 848,483

[22] Filed: Apr. 7, 1986

[30] Foreign Application Priority Data

Apr. 18, 1985 [JP] Japan .................................. 60-81360

[51] Int. Cl.$^4$ ........................................... A61K 31/195
[52] U.S. Cl. ................................................. 514/561
[58] Field of Search ........................ 514/561; 562/567

[56] References Cited

U.S. PATENT DOCUMENTS 3,112,341 11/1963 Tatsuoka et al. .................. 562/567

OTHER PUBLICATIONS

"Hon, A New Antibiotic Produced by *Streptomyces akiyoshiensis* Nov. SP", *The Journal of Antibiotics.* Ser. A, Jan. 1961, vol. XIV, No. 1, pp. 39–43.

179. Akira Miyake: δ–Hydroxy–γ–oxo–L–Norvaline, A New Antitubercular Antibiotic, vol. 8, (1960), pp. 1071–1073.

*Primary Examiner*—Leonard Schenkman
*Attorney, Agent, or Firm*—Pahl, Lorusso & Loud

[57] ABSTRACT

Method for the treatment of systemic mycosis of mammals comprises administering (S)-2-amino-5-hydroxy-4-oxopentanoicacid in a therapeutically effective amount to said mammals suffering from mycosis, typically candidosis.

2 Claims, No Drawings

METHOD FOR THE TREATMENT OF SYSTEMIC MYCOSIS

BACKGROUND OF THE INVENTION

This invention relates to a novel method for the treatment of systemic mycosis. More particularly, it is concerned with a method for the treatment of systemic mycosis which comprises administering an active compound, (S)-2-amino-5-hydroxy-4-oxopentanoicacid.

Under the present circumstances, only a limited number of antimycotic agents are available for the treatment of systemic mycoses. Such drugs currently marketed are as follow: the polyene antibiotic amphotericin B; the pyrimidine analog flucytosine; and the imidazole derivatives miconazole and ketoconazole. All of these drugs are far from ideal because they have problems with their limited antimicrobial spectrum and effectiveness, toxicity and side effects, unfavorable pharmacokinetics and/or development of resistance. Thus, unlike therapy for bacterial infections, very few and unsatisfactory therapeutic agents have been developed for the treatment of infections caused by fungi. This appears to be mainly due to the fact that like humans and animals, fungi are eukaryotic, and it has been difficult to develop antimycotic agents that have the selectivity to mycotic structures and metabolic processes that antibacterial agents have for bacteria.

Systemic mycoses are now becoming more important in clinical practice. This is due in major part to the rising incidence of serious mycoses among compromized patients. Candidiasis is the infection most often encountered in such patients that is followed by aspergillosis and cryptococcosis.

Despite the drawbacks and limitations of the above-mentioned antimycotic agents, they are all that are available for the treatment of the patients with systemic mycoses.

The present inventors have made intensive studies to develop a more desirable antimycotic agent useful for the treatment of systemic mycosis and, as a result, they have discovered a compound which has a potent antimycotic activity without appreciable toxicity.

It is, accordingly, a primary object of this invention to provide a method using of (S)-2-amino-5-hydroxy-4-oxopentanoicacid as antimycotic agent.

BRIEF SUMMARY OF THE INVENTION

The present invention provides a method for the treatment of systemic mycosis which comprises administering (S)-2-amino-5-hydroxy-4-oxopentanoicacid in a therapeutically effective amount to said mammals suffering from mycosis.

DETAILED DESCRIPTION OF THE INVENTION

The (S)-2-amino-5-hydroxy-4-oxopentanoicacid which may be employed for the present method for the treatment of systemic mycosis is a substance known per se and can be obtained, for example, by isolation and purification of the cultured broth of *Streptomyces akiyoshiensis* as disclosed by S. Tatsuoka et al. in the Journal of Antibiotics Ser. A, 14, 39 (1961) or, alternatively, by a synthetic process as disclosed by A. Miyake in Chem. Pharm. Bull., 8, 1074 (1960).

According to the report by A. Miyake in Chem. Pharm. Bull., 8, 1071 (1960), this substance is highly active against pathogenic human tubercle bacilli, but does hardly exert an in vitro antimycotic activity.

However, the present inventors have unexpectedly found that this substance has a significant protective and therapeutic efficacy in mice experimentally infected with *Candida albicans*. This finding leads the inventors to possible usefulness of this substance for the therapy of human cases of candidiasis and other systemic mycoses. This substance is an extremely specific antimycotic agent in that it quite differs in chemical structure from any existing antimycotic agents. This substance is also characterized by a very high tolerability in experimental animals as demonstrated by the following data on acute toxicity.

| Acute Toxicity in Mice: $LD_{50}$ (mg/kg) | | |
| --- | --- | --- |
| p.o. | i.p. | s.c. |
| $\geq 6,000$ | $\geq 5,000$ | $\geq 5,000$ |

The results imply that the toxicity of this substance is lower than that of any existing antimycotic drugs.

The therapeutic efficacy of the active compound in this invention, (S)-2-amino-5-hydroxy-4-oxopentanoicacid, can be achieved by oral or parenteral administration, but is optimally exhibited when the oral route of administration is employed. Although the dosage of this compound should be determined on the basis of age of the patient, type and severity of infections and some other conditions, the recommended daily dosage for an adult human will be in the range from 300 to 12,000 mg in single to three divided doses.

The pharmaceutical composition containing (S)-2-amino-5-hydroxy-4-oxopentanoicacid may be formulated in the form of any suitable preparation, e.g., a tablet, capsule, granule, syrup, injectable solution or drop infusion according to a method known per se. For instance, such preparations as a capsule, tablet or granule may be formulated by using any conventional excipients or carriers, e.g., crystalline cellulose, hydroxypropylcellulose, talc, lactose, light anhydrous silicic acid and others.

The present antimycotic compound may be applied alone or in combination with some other antimycotic drug for successful treatment of systemic mycosis.

Because of the low toxicity, the present antimycotic compound may be administered consecutively for a long period of time at large dosages with successful therapeutic results. Thus, the present antimycotic compound may be useful not only for therapy but also for prophylaxis of systemic mycosis in those patients who have received some surgical treatments such as organ transplantation and prosthesis of heart valve. From the foregoing points of view, the present antimycotic compound may apparently have an increased practicability as compared with all the existing antimycotic drugs.

This invention will be further illustrated by way of the following Test Examples and Preparation Examples, but they are not contemplated to be limiting the scope of this invention.

TEST EXAMPLE 1

Female SPF mice Crj:CD-1 (ICR) strain, 4 weeks of age, weighing 18 g±1 g, were used as test animals. One loopful organisms of *Candida albicans* TIMM 0239 grown on Sabouraud's glucose agar slants were inoculated into Sabouraud's glucose broth containing 0.5% yeast extract. Then cultures were grown aerobically at 37° C. for 18 hours. The organisms were harvested from the cultures, washed twice with sterilized physiological saline, and finally suspended in saline. A total number of organisms was counted in a Burker-Turk hemocytometer. Thus prepared cell suspension was adjusted to contain $10^6$ cells/ml, 0.2 ml of which was then injected into the tail vein in each mouse. Infected mice were allocated randomly to different groups. Each group consisted of eight mice.

(S)-2-amino-5-hydroxy-4-oxopentanoicacid was dissolved in sterilized physiological saline. The mice in the treated groups received the solution of this compound in a dose of 50 mg per kg mouse body weight once daily via an intravenous, subcutaneous, intraperitoneal or oral route for 5 consecutive days, starting on the day of infection. The first treatment was given immediately after a challenge of *Candida albicans*. The untreated control animals were intravenously given the same volume of saline in place of the test compound solution. The animals were observed daily for 10 days postinfection. The results of this experiment are summarized in Table 1.

TABLE 1

| Groups | Route of administration | Treatment period (day) | Survival rate |
|---|---|---|---|
| Control | intravenous | 5 | 0/8 |
| Treated | intravenous | 5 | 4/8 |
| Treated | subcutaneous | 5 | 0/8 |
| Treated | intraperitoneal | 5 | 0/8 |
| Treated | oral | 5 | 4/8 |

TEST EXAMPLE 2

The same experimental conditions as for Test Example 1 were employed, except that all groups of five animals were infected with $1.0 \times 10^6$ organisms and treated with either 25, 50 or 100 mg/kg of the test compound twice daily for 14 consecutive days. Duration of observation period was two weeks after infection.

The criteria to evaluate efficacy of the test compound include survival rate and viable counts of *Candida albicans* recovered from the kidneys of infected animals. Both kidneys were excised from all the animals at the end of the experimental period, homogenized and cultured on Sabouraud's glucose agar plates for assay of viable counts. Cultures were also performed with the same organ after necropsy of the animals that did not survive the whole experimental period.

The results of the experiment are summarized in Table 2.

TABLE 2

| Groups | Route of administration | Therapeutic dose (mg/kg) | Treatment period (days) | Survival rate | Average viable counts recovered (per mouse) |
|---|---|---|---|---|---|
| Control | oral | — | 14 | 0/5 | $4.87 \times 10^7$ |
| Treated | oral | 25 | 14 | 1/5 | $1.45 \times 10^7$ |
| Treated | oral | 50 | 14 | 2/5 | $1.41 \times 10^6$ |
| Treated | oral | 100 | 14 | 5/5 | $2.41 \times 10^5$ |

As can be seen from the results of Test Example 1, the present antimycotic compound can show a significant therapeutic efficacy, especially when it was administered by the intravenous or oral route in murine models of systemic candidiasis. As can be seen from the results of Test Example 2, a close correlation is observed between therapeutic efficacy and oral dose of this compound. Moreover, mice surviving Candida infection that received the compound in a dose of 100 mg/kg in Test Example 2 showed a very healthy appearance over the experimental period which is comparable to that of uninfected normal mice. It suggests that the present antimycotic compound has an excellent therapeutic effectiveness against systemic candidiasis in mice and that the compound is favorably tolerated by the animals.

PREPARATION EXAMPLE 1 (TABLETS)

Tablets containing (S)-2-amino-5-hydroxy-4-oxopentanoicacid at 500 mg per tablet and having the following formulation are prepared according to a method well known per se.

| | |
|---|---|
| (S)—2-Amino-5-hydroxy-4-oxopentanoicacid | 500 mg |
| Low-substituted hydroxypropylcellulose | 50 mg |
| Crystalline cellulose | 60 mg |
| Lactose | 60 mg |
| Light anhydrous silicic acid | 20 mg |
| Talc | 20 mg |
| Per one tablet | 710 mg |

PREPARATION EXAMPLE 2 (CAPSULES)

Capsules containing (S)-2-amino-5-hydroxy-4-oxopentanoicacid at 500 mg per capsule and having the following formulation are prepared according to a method well known per se.

| | |
|---|---|
| (S)—2-Amino-5-hydroxy-4-oxopentanoicacid | 500 mg |
| Crystalline cellulose | 150 mg |
| Lactose | 150 mg |
| Light anhydrous silicic acid | 20 mg |
| Talc | 20 mg |
| Per one capsule | 840 mg |

PREPARATION EXAMPLE 3 (GRANULES)

Granules containing (S)-2-amino-5-hydroxy-4-oxopentanoicacid at 1,000 mg per package and having the following formulation are prepared according to a method well known per se.

| | |
|---|---|
| (S)—2-Amino-5-hydroxy-4-oxopentanoicacid | 1,000 mg |
| Lactose | 700 mg |
| Hydroxypropylcellulose | 30 mg |
| Talc | 10 mg |
| Per one package | 1,740 mg |

PREPARATION EXAMPLE 4 (SYRUP)

A syrup containing 2,000 mg of (S)-2-amino-5-hydroxy-4-oxopentanoicacid and having the following formulation is prepared according to a method well known per se.

| | |
|---|---|
| (S)—2-Amino-5-hydroxy-4-oxopentanoicacid | 2,000 mg |
| Simple syrup | 50 ml |
| Purified water ad libitum to make up a total volume to | 100 ml |

PREPARATION EXAMPLE 5 (INTRAVENOUS DRIP INFUSION PREPARATION)

An intravenous drip infusion preparation is prepared by dissolving 2,000 mg of (S)-2-amino-5-hydroxy-4-oxopentanoicacid in 500 ml of a physiologically acceptable electrolyte solution.

What is claimed is:

1. A method for the treatment of candidiasis in mammals which comprises administering (S)-2-amino-5-hydroxy-4-oxopentanoicacid in a therapeutically effective amount to said mammals suffering from candidiasis.

2. A method for the treatment of candidiasis in mammals as claimed in claim 1, wherein said administration is orally in a daily dose for an adult human in the range from 300 to 12,000 mg in single to three divided doses.

* * * * *